US012522795B2

(12) United States Patent
Raghavan et al.

(10) Patent No.: US 12,522,795 B2
(45) Date of Patent: Jan. 13, 2026

(54) 3D RAPID PROTOTYPABLE TUNABLE PERISTALSIS BIOREACTOR

(71) Applicant: The Texas A&M University System, College Station, TX (US)

(72) Inventors: Shreya Raghavan, Cypress, TX (US); Logan Zane Crawford, College Station, TX (US)

(73) Assignee: The Texas A&M University System, College Station, TX (US)

( * ) Notice: Subject to any disclaimer, the term of this patent is extended or adjusted under 35 U.S.C. 154(b) by 787 days.

(21) Appl. No.: 17/869,530

(22) Filed: Jul. 20, 2022

(65) Prior Publication Data

US 2023/0025737 A1 Jan. 26, 2023

Related U.S. Application Data

(60) Provisional application No. 63/223,710, filed on Jul. 20, 2021.

(51) Int. Cl.
*C12M 1/42* (2006.01)

(52) U.S. Cl.
CPC .................................. *C12M 35/04* (2013.01)

(58) Field of Classification Search
CPC ............................. C12M 23/34; C12M 35/04
See application file for complete search history.

(56) References Cited

U.S. PATENT DOCUMENTS 4,906,577 A * 3/1990 Armstrong ............ C12M 23/38
435/295.3
2021/0230532 A1* 7/2021 Lee ..................... C12N 5/0662

* cited by examiner

*Primary Examiner* — Michael L Hobbs
*Assistant Examiner* — Lenora A Abel
(74) *Attorney, Agent, or Firm* — Jackson Walker LLP

(57) ABSTRACT

In an embodiment, the present disclosure pertains to a bioreactor. In some embodiments, the bioreactor includes an inlet and an outlet, a chamber having a wall and a cell area, and a screw drive. In some embodiments, the inlet and the outlet are in fluid communication via the chamber. In a further embodiment, the present disclosure pertains to a method of modeling peristalsis. In some embodiments, the method applying at least one of axial strain, multi-axial strain, or shear stress to a wall within a bioreactor of the present disclosure, and measuring mechanical forces applied on the wall via the screw drive.

20 Claims, 7 Drawing Sheets

3D RAPID PROTOTYPABLE TUNABLE PERISTALSIS BIOREACTOR

CROSS-REFERENCE TO RELATED APPLICATIONS

This patent application claims priority from, and incorporates by reference the entire disclosure of, U.S. Provisional Application 63/223,710 filed on Jul. 20, 2021.

TECHNICAL FIELD

The present disclosure relates generally to bioreactors and more particularly, but not by way of limitation, to three-dimensional (3D) rapid prototypable tunable peristalsis bioreactors.

BACKGROUND

This section provides background information to facilitate a better understanding of the various embodiments of the disclosure. It should be understood that the statements in this section of this document are to be read in this light, and not as admissions of prior art.

Current in vitro model systems applied to various organs suffer from shortcomings in their representation of peristalsis. Mainly, the current models simplify kinematics to either shear stress or uniaxial strain; neither of which are adequately representative of the complex dynamics of peristaltic patterns. Various embodiments of the present disclosure seek to address the aforementioned shortcomings.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to a bioreactor. In some embodiments, the bioreactor includes an inlet and an outlet, a chamber having a wall or membrane, a cell area, and a screw drive. In some embodiments, the inlet and the outlet are in fluid communication via the chamber.

In some embodiments, the bioreactor further includes a first region and a second region. In some embodiments, the first region houses the inlet and the second region houses the outlet. In some embodiments, the first region is movable along a first variable axis and the second region is movable along a second variable axis. In some embodiments, indirect forces caused by rotation of the screw drive move the first region about the first movable axis and the second region about the second movable axis to thereby mimic peristalsis. In some embodiments, the peristalsis includes at least one of multi-axial wall strain or pulsatile fluid flow. In some embodiments, a portion of the chamber is patterned. For example, one or more walls of the chamber may be textured/patterned.

In some embodiments, the portion of the chamber is a top portion. In some embodiments, a height of the chamber is variable. In some embodiments, a variable height of the chamber is in the form of an arch. In some embodiments, the screw drive includes threads. In some embodiments, the threads include at least one of a height, a thickness, or a pitch to thereby mimic peristalsis. In some embodiments, the bioreactor further includes a peristaltic pump. In some embodiments, a combination of the peristaltic pump and the screw drive deliver multiaxial strain and concurrent shear stress to the wall/membrane. In some embodiments, the bioreactor further includes a motor operably connected to the screw drive to provide axial rotation of the screw drive about an axis.

In some embodiments, the chamber and screw drive are configured to emulate kinematics in an organ that can include, without limitation, an intestine, a gastrointestinal tract, a urinary tract, a reproductive system tract, cylindrical organs or tracts, and combinations thereof. In some embodiments, design of at least one of the screw drive, the chamber, the wall/membrane, or the cell area is informed via computational modeling. In some embodiments, the design includes tunability. In some embodiments, the design includes peristalsis modeling that can mimic mechanical forces observed across multiple organ systems.

In some embodiments, mechanical forces are applied via the screw drive. In some embodiments, the wall/membrane is operable to receive and transmit the mechanical forces to biological elements.

In a further embodiment, the present disclosure pertains to a method of modeling peristalsis. In some embodiments, the method applying at least one of axial strain, multi-axial strain, or shear stress to a wall/membrane within a bioreactor of the present disclosure, and measuring mechanical forces applied on the wall via the screw drive.

BRIEF DESCRIPTION OF THE DRAWINGS

A more complete understanding of the subject matter of the present disclosure may be obtained by reference to the following Detailed Description when taken in conjunction with the accompanying Drawings wherein.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Peristalsis is a nuanced mechanical stimulus including multi-axial strain (radial and axial strain) and shear stress. Peristalsis is central to many smooth muscle organs including the gastrointestinal tract, uterus and ureters. Forces associated with peristalsis, therefore, regulate diverse biological functions including digestion, male and female reproductive function, and urine dynamics. Given the central role peristalsis plays in physiology, it is imperative that in vitro studies of development and disease include peristalsis.

Current in vitro model systems suffer from various shortcomings in their representation of peristalsis. Mainly, they simplify kinematics to either shear stress or uniaxial strain; neither of which are adequately representative of the complex dynamics of peristaltic patterns. Appropriately mimicking both forces concurrently is important because several cell types respond differently to shear stress and strain. Therefore, an objective of this disclosure is a bioreactor capable of mimicking peristalsis holistically. A novel actuating screw-drive based design combined with a peristaltic pump was engineered in order to deliver multiaxial strain and concurrent shear stress to a biocompatible Polydimethylsiloxane (PDMS) membrane "wall". Using this bioreactor, it was demonstrated that human mesenchymal stem cells (hMSCs) respond to peristalsis differently than perfusion or strain.

Figure 1:
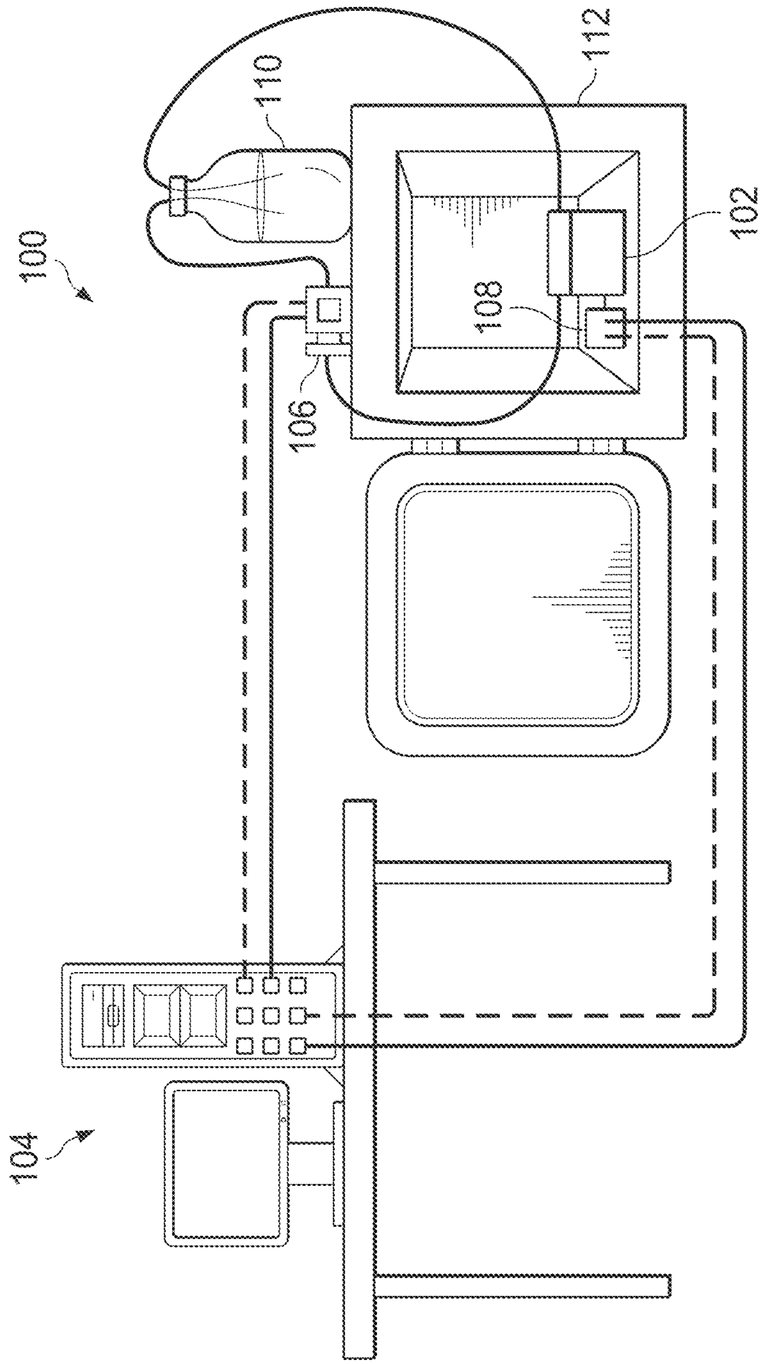
FIG. 1 illustrates a peristaltic bioreactor system according to embodiments of the disclosure.

FIG. 1 illustrates a peristaltic bioreactor system 100 according to embodiments of the disclosure. System 100 includes a bioreactor 102. A computer 104 is in electrical communication with and controls a peristaltic pump 106 and a motor 108. Computer 104 includes a processor and memory and is configured to control operating parameters of peristaltic pump 106 and motor 108 (e.g., speed). Peristaltic pump 106 is configured to pump media through bioreactor 102. The media may be drawn out of a reservoir 110 by peristaltic pump 106, passed through bioreactor 102, and then returned to reservoir 110. Motor 108 is coupled to an actuating screw (e.g., see FIG. 3A), the combination of which form a screw drive. The actuating screw is disposed within bioreactor 102 and will be discussed in more detail below. System 100 may also include an incubator 112 that houses bioreactor 102 during operation. Incubator 112 allows for a temperature of bioreactor 102 to be controlled.

Figure 2:
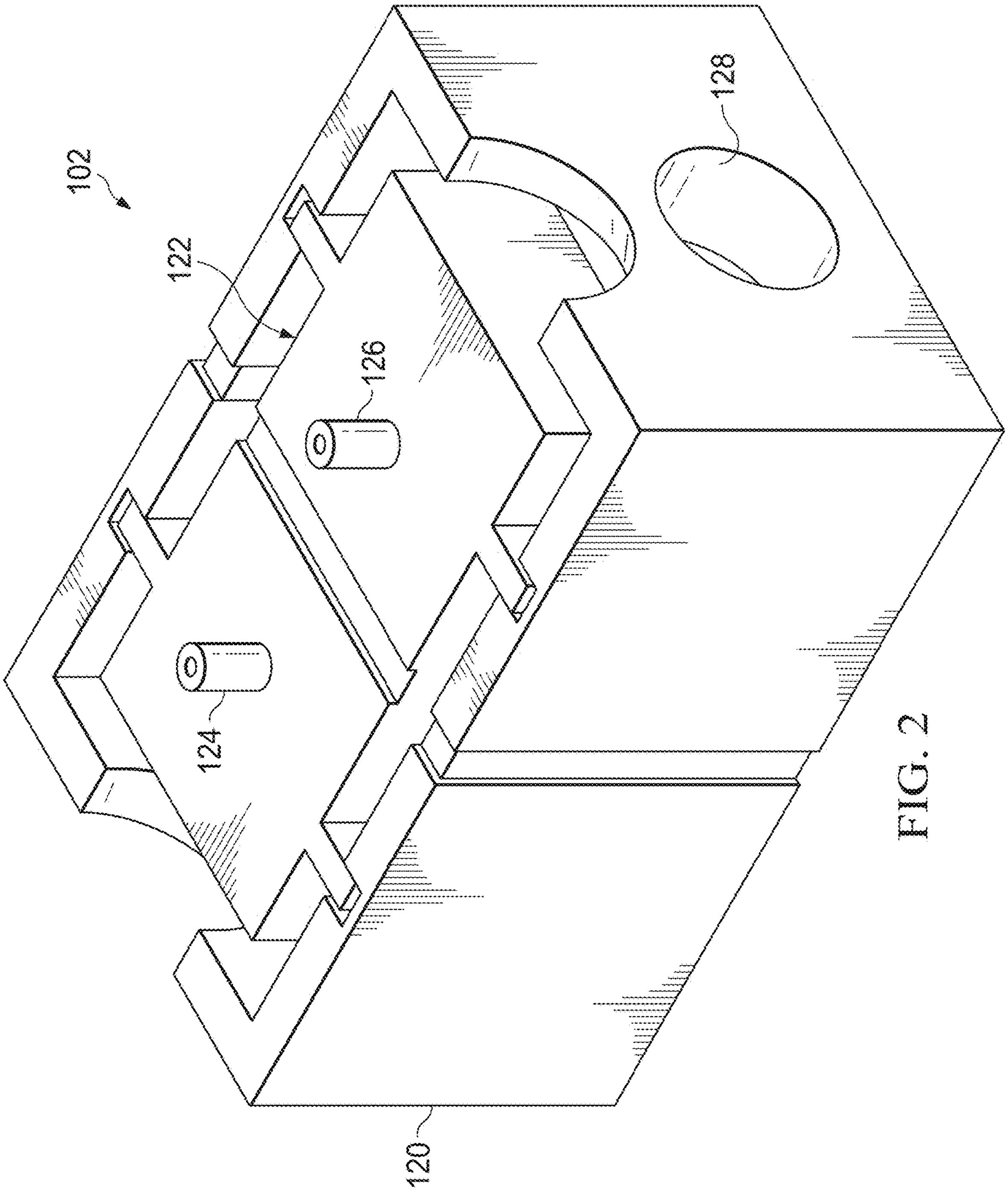
FIG. 2 is a perspective view of a bioreactor according to embodiments of the disclosure.

FIG. 2 is a perspective view of bioreactor 102 according embodiments of the disclosure. Bioreactor 102 includes a housing 120 in which there is a chamber top 122. Chamber top 122 includes an inlet 124 and an outlet 126 that allow media pumped from peristaltic pump 106 to flow through bioreactor 102. An area proximal to inlet 124 defines a first region of chamber top 122 and an area proximal to outlet 126 defines a second region. Housing 120 includes a bore 128 through which a drive shaft of motor 108 may pass to connect to the actuating screw (e.g., see FIG. 3A). In the embodiment shown in FIG. 2, bioreactor 102 is 3D printed, with chamber top 122 being a separate part from housing 120. Manufacturing bioreactor 102 from separable components assists with assembly of bioreactor 102 as the actuating screw may be more easily placed into chamber top 122. In other embodiments, bioreactor 102 may be made with other manufacturing techniques.

Figure 3A:
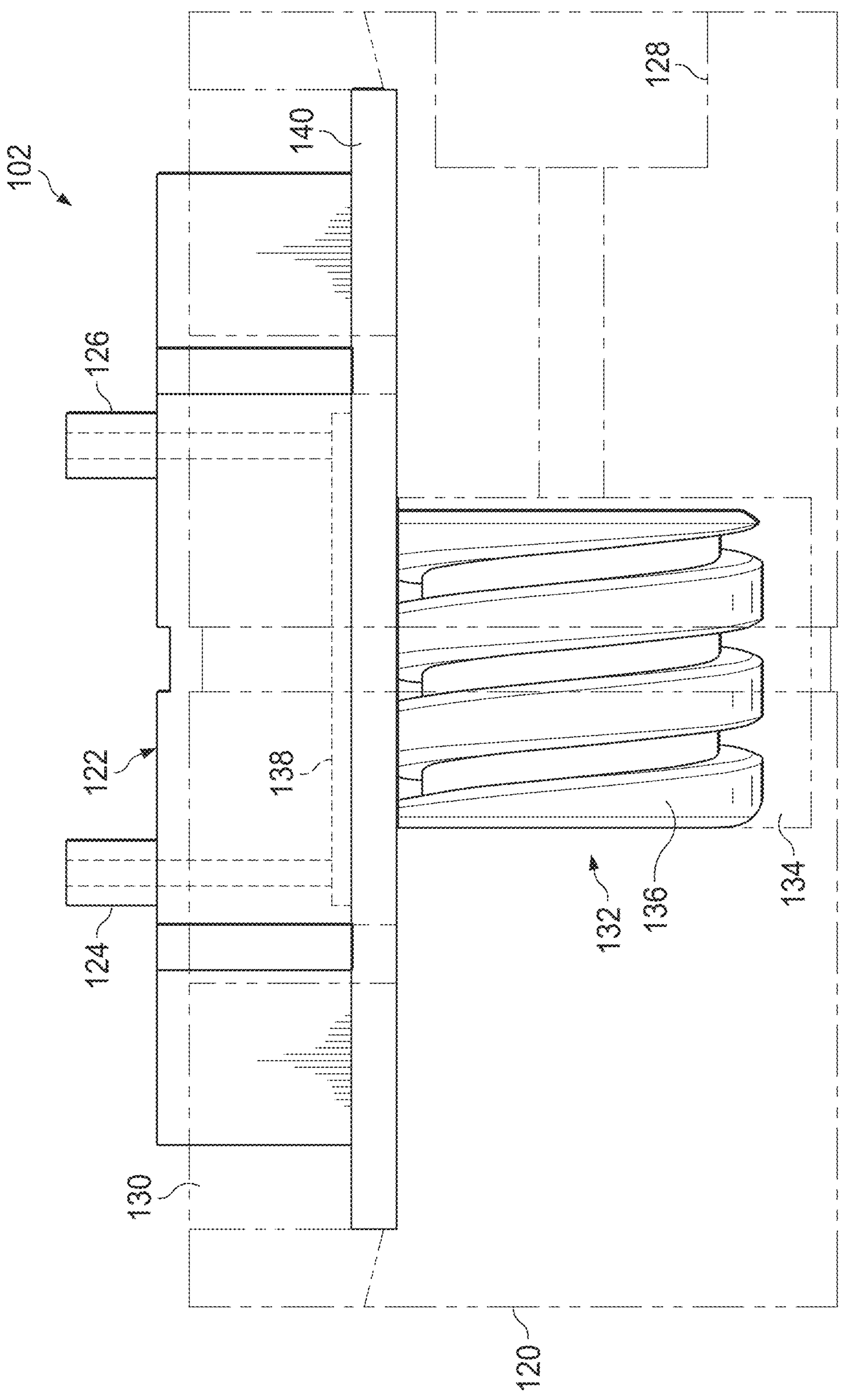
FIGS. 3A-3C are side, top, and front views, respectively, of a bioreactor according to embodiments of the disclosure.
Figure 3B:
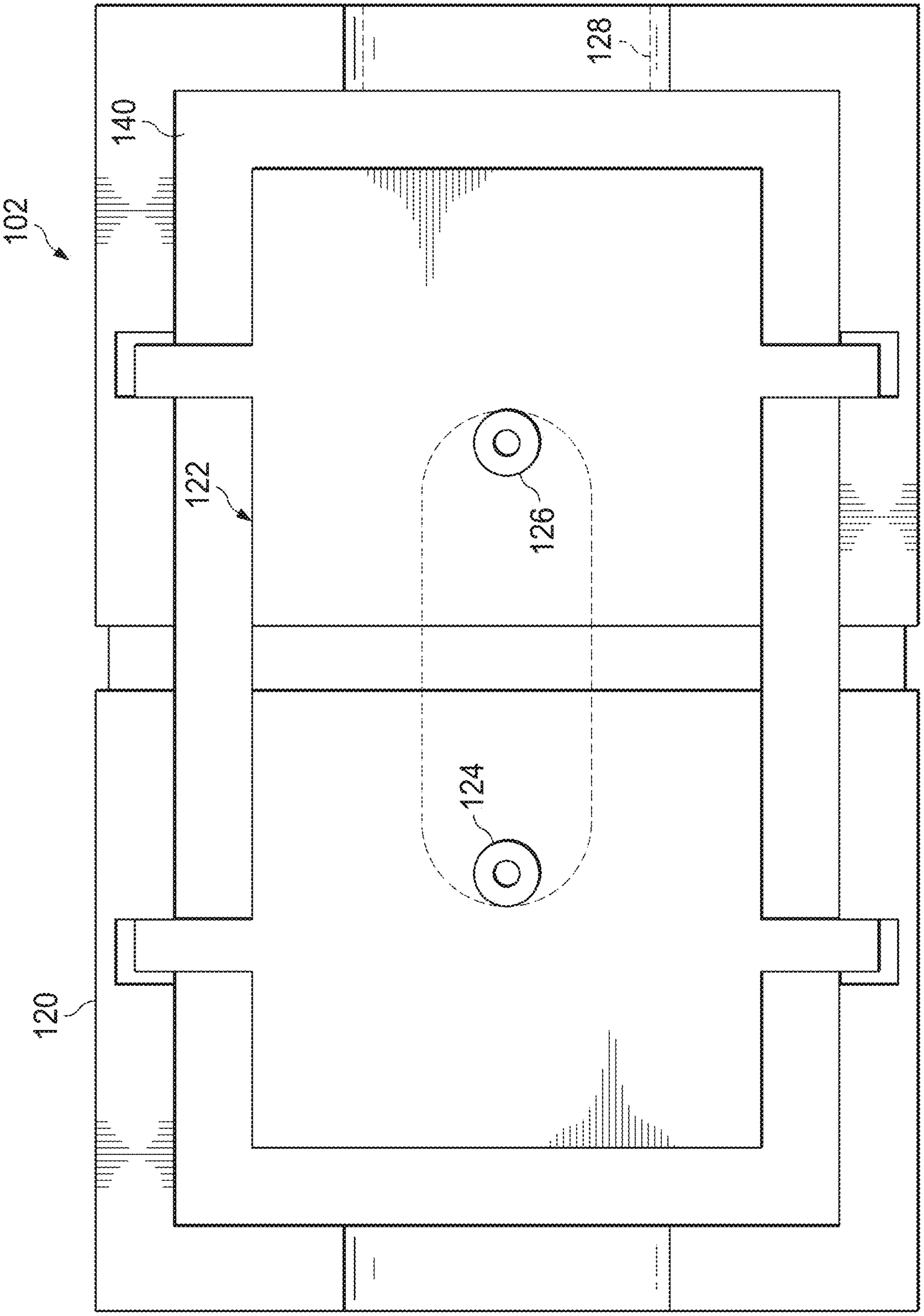
Figure 3C:
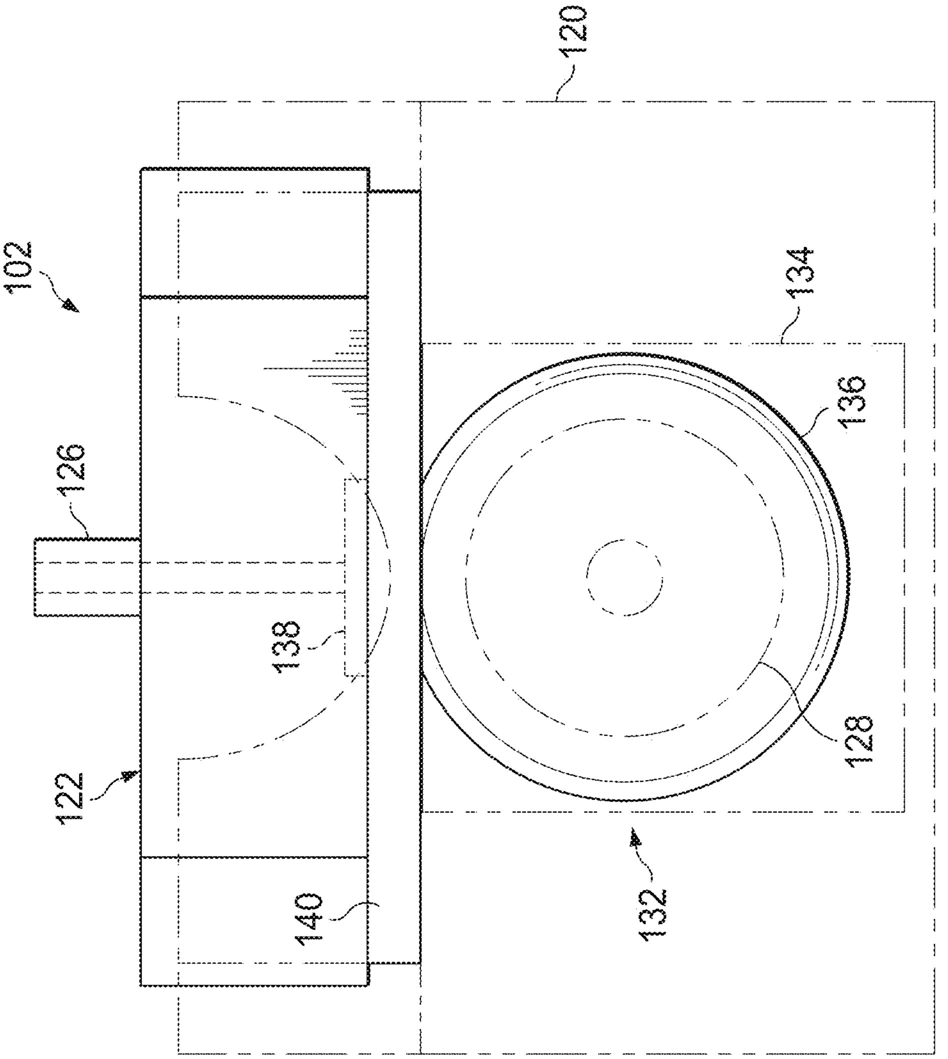

FIGS. 3A-3C are side, top, and front views, respectively, of bioreactor 102 according to embodiments of the disclosure. Housing 120 has been made transparent to allow the inside of bioreactor 102 to be better seen. Chamber top 122 is configured to sit within an upper portion 130 of housing 120. A sealed chamber 132 is formed in the space between housing 120 and chamber top 122. Sealed chamber 132 is fluidly coupled with inlet 124 and outlet 126 to allow media to pass therethrough. Sealed chamber 132 includes a screw chamber 134 that houses actuating screw 136 and a cell chamber 138. In some embodiments, a height of cell chamber 138 is variable to change a volume thereof. In some embodiments, an upper portion of cell chamber 138 is in the form of an arch (e.g., similar to FIG. 4). Actuating screw 136 incudes threads having a height, thickness, and pitch that, during operation, mimic peristalsis.

Screw chamber 134 and cell chamber 138 are separated by a membrane 140. A smaller bore is concentric with bore 128 and extends between screw chamber 134 and bore 128 to accommodate the drive shaft of motor 108. In some embodiments, bioreactor 102 is used in connection with a peristaltic pump (e.g., pump 106). In some embodiments, a combination of the peristaltic pump and the screw drive deliver multiaxial strain and concurrent shear stress to the wall. In some embodiments, the bioreactor further includes a motor operably connected to the screw drive to provide axial rotation of the screw drive about an axis.

Figure 4:
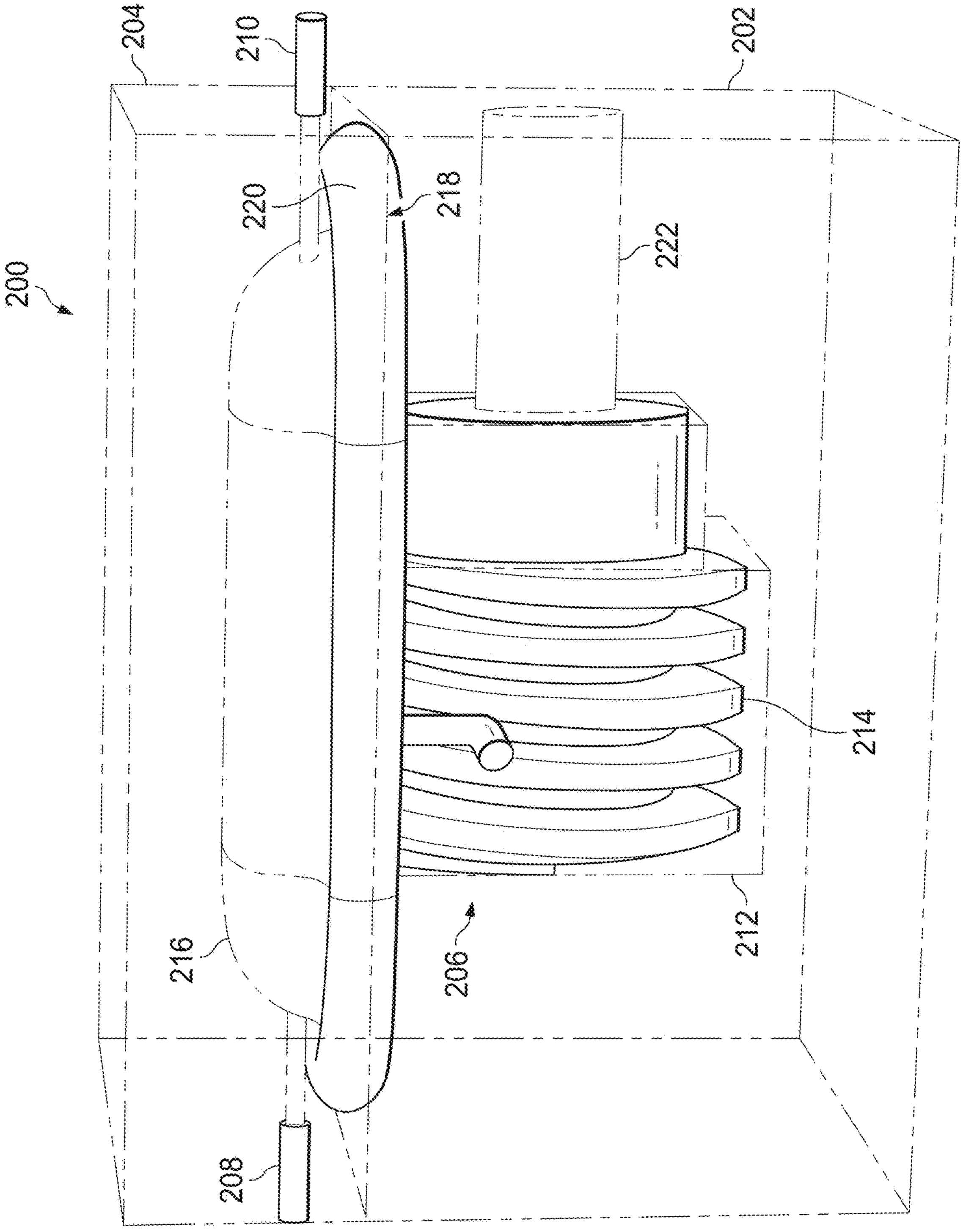
FIG. 4 is perspective of a bioreactor with a housing of the bioreactor partially hidden according to embodiments of the disclosure.
Figure 5C:
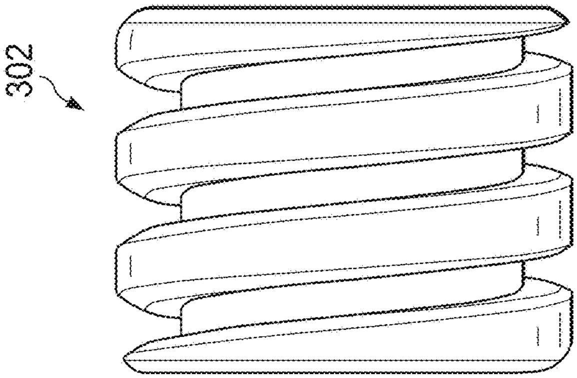
FIGS. 5A-5C illustrate different designs for an actuating screw according to embodiments of the disclosure.
Figure 5B:
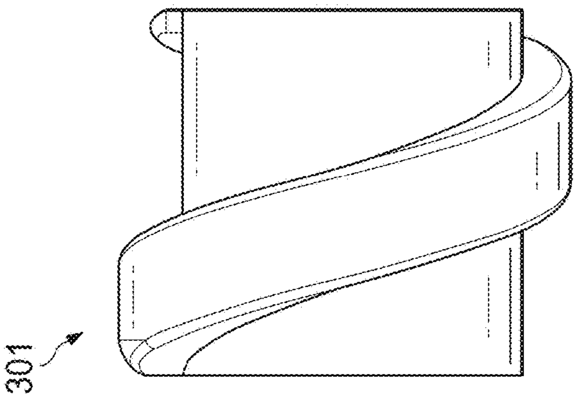
Figure 5A:
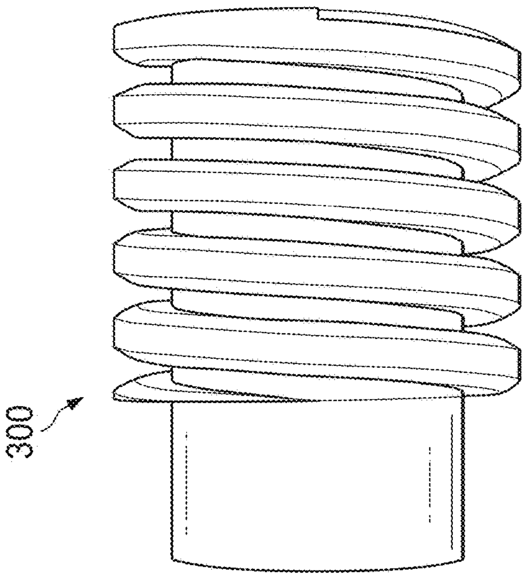

FIG. 4 is a perspective of a bioreactor 200 with a housing 202 and a chamber top 204 partially hidden to better show an inside of bioreactor 200 according to embodiments of the disclosure. Bioreactor 200 is similar in function to bioreactor 102 apart from a few differences in dimensions and inlet/outlet locations. Operation of bioreactor 200 is nonetheless similar to bioreactor 102. A sealed chamber 206 is formed in an internal space between housing 202 and chamber top 204. Sealed chamber 206 is fluidly coupled with an inlet 208 and an outlet 210 to allow media to pass therethrough. In contrast to inlet 124 and outlet 126 of bioreactor 102, inlet 208 and outlet 210 of bioreactor 200 are oriented horizontally instead of vertically. It will be appreciated that the inlets/outlets of bioreactors 102/200 may be oriented in a variety of ways. Sealed chamber 206 includes a screw chamber 212 that houses an actuating screw 214 and a cell chamber 216. Screw chamber 212 and cell chamber 216 are separated by a membrane 218. Compared to bioreactor 102, cell chamber 216 of bioreactor 200 is arched and provides a greater internal volume. Membrane 218 includes an o-ring 220 around its periphery that helps seal housing 202 and chamber top 204. A bore 222 extends through housing 202 and accommodates the drive shaft from a motor (e.g., motor 108) for rotating actuating FIGS. 5A-5C illustrate different designs for actuating screws 300, 301, and 302, respectively, according to embodiments of the disclosure. The design of actuating screws for use in bioreactors of the instant disclosure may be tuned by altering various parameters of the actuating screw such as, for example, pitch, thread rotations, thread length, thread coarseness, shaft diameter, and thread height. Changing parameters of the actuating screw changes the strain experienced by the membrane of the bioreactor. Depending on which organ/environment is being modeled, the parameters of the actuating screw may be selected to more closely mimic the desired organ/environment.

Reference will now be made to more specific embodiments of the present disclosure and data that provides support for such embodiments. However, it should be noted that the disclosure below is for illustrative purposes only and is not intended to limit the scope of the claimed subject matter in any way.

Materials and Methods. Peristalsis kinematics (strain and shear stress) for the bioreactor were determined using finite element modeling, which were then validated experimentally using a piezoelectric poly-dopamine based hydrogel. hMSCs were seeded onto the membrane of the and subjected to strain, perfusion, or peristalsis, or maintained as static controls. Cells were then assayed for gene expression changes using Real-Time Polymerase Chain Reaction (qRT-PCR) and changes in proliferation and actin filament alignment via immunofluorescence.

Results and Discussion. Preliminary computational modeling of the bioreactor indicated that the radial indentation of the actuating screw into the membrane and subsequent rotation and fluid flow results in peristaltic motion in the membrane. Experimental measurements of strain using resistivity of piezoelectric hydrogels resulted in close alignment of experimental and model-predicted values (15.9±4.2% experimental strain vs. 15.2% predicted). Cellular studies with hMSCs indicated significantly different effects in the expression of transgelin, aggrecan I, elastin and collagen IV across all conditions. Elastin and aggrecan I both showed a >0.4-fold increased expression in peristalsis compared to both strain and perfusion. Expression trends were similar for both genes illuminating the force specific effects in genetic markers of differentiation and cellular response. Additionally, increased expression of transgelin decreases cell proliferation but increases differentiation. This indicates that the peristalsis and perfusion conditions are differentiating but not proliferating, relative to the control. These findings were further confirmed via proliferation quantification of Ki67 where peristalsis had a 40% decrease and perfusion had a 20% decrease in proliferating cells compared to the control. Strain analysis also indicated a 45% decrease in proliferation compared to the control. Additionally, the down-regulation in FGF2 across all conditions indicates a decrease in cell proliferation which is consistent with the Ki67 quantification. When actin fiber alignment was characterized, static controls were randomly oriented. The application of perfusion or shear promoted >40% of fiber alignment along one axis. Additionally, the application of peristalsis resulted in higher circularity, and therefore an even distribution of fiber alignment uniformly across 0-180°, illustrating the ability of cells to align in response to concurrent multi-axial strain and shear stress.

Conclusions. Collectively, this data suggests that the peristalsis bioreactor is capable of generating concurrent multi-axial strain and shear stress on the membrane to mimic real-world conditions. hMSCs experience peristalsis differently than perfusion or strain, resulting in changes in proliferation, actin fiber organization and genetic markers of differentiation. Future goals involve demonstrating the applicability of this device to the study of the intestinal tract. Importantly, due to the tunability of this device, this system can be applied to various organ systems lending application to a multitude of diseases and disorders.

As described above, the present disclosure relates to various bioreactors capable of applying controlled strain (on at least two different axes) and shear forces, simultaneously or individually. The mechanical forces are applied via a uniquely designed screw drive, and the design houses a 'wall' like surface that is capable of receiving and transmitting this mechanical force to biological elements.

In general, bioreactors designed with the intention of studying peristalsis have two fundamental limitations. First, peristalsis itself is simplified to relying either solely on perfusion-based fluid shear, or uniaxial cyclic strain. Second, platforms are seldom agnostic of biological applicability, that is, they are designed for specific organs. Urothelial tissue engineering bioreactors, for example, are used to precondition ureteral grafts prior to implantation, which results in urothelial cellular organization. The mechanical stimulus however is either fluid flow or cyclic stretching, neither of which are biomimetic of ureteric peristalsis. Peristalsis bioreactors for the intestine far outnumber other organs both at the microfluidic and macro biologic levels. In fact, some of these models even advantageously represent the hollow tubular nature of the gastrointestinal tract itself. However, these models are applicable to the intestine alone, with no room to alter peristaltic patterns. Instances of peristalsis bioreactors within the reproductive tract are much fewer and far between, with models relying on fluid shear stress from perfusion, or uniaxial cyclic tensile stretch.

Disclosed herein, are novel tunable peristalsis bioreactors in which the design is informed via computational modeling. The design incorporates 'tunability', where the peristalsis bioreactor can mimic mechanical forces observed in multiple organ systems. Using intestinal peristalsis as a test case, the validity and clinical utility of the peristalsis bioreactor in mimicking the kinematics of peristalsis was demonstrated.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the embodiments of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A bioreactor comprising:
an inlet and an outlet;
a cell chamber in fluid communication with the inlet and the outlet;
a screw chamber separated from the cell chamber by a membrane; and
a screw drive disposed within the screw chamber,
wherein the screw drive is configured to apply at least one of axial strain, multi-axial strain, or shear stress to the membrane.

2. The bioreactor of claim 1, further comprising a first region and a second region, wherein the first region houses the inlet and the second region houses the outlet.

3. The bioreactor of claim 2, wherein the first region is movable along a first variable axis and the second region is movable along a second variable axis.

4. The bioreactor of claim 3, wherein indirect forces caused by rotation of the screw drive move the first region about the first movable axis and the second region about the second movable axis to thereby mimic peristalsis.

5. The bioreactor of claim 4, wherein the peristalsis comprises at least one of multi-axial wall strain or pulsatile fluid flow.

6. The bioreactor of claim 1, wherein a portion of the cell chamber is patterned.

7. The bioreactor of claim 6, wherein the portion of the cell chamber is a top portion.

8. The bioreactor of claim 1, wherein a height of the cell chamber is variable.

9. The bioreactor of claim 8, wherein the variable height of the cell chamber is in the form of an arch.

10. The bioreactor of claim 1, wherein the screw drive comprises threads.

11. The bioreactor of claim 10, wherein the threads comprise at least one of a height, a thickness, or a pitch to thereby mimic peristalsis.

12. The bioreactor of claim 1, further comprising a peristaltic pump in fluid communication with the inlet and the outlet.

13. The bioreactor of claim 12, wherein a combination of the peristaltic pump and the screw drive deliver multiaxial strain and concurrent shear stress to the membrane.

14. The bioreactor of claim 1, further comprising a motor operably connected to the screw drive to provide axial rotation of the screw drive about an axis.

15. The bioreactor of claim 1, wherein the cell chamber and screw drive are configured to emulate kinematics in an organ selected from the group consisting of an intestine, a gastrointestinal tract, a urinary tract, a reproductive system tract, cylindrical organs or tracts, and combinations thereof.

16. The bioreactor of claim 1, wherein design of at least one of the drive screw, the cell chamber, and the membrane is informed via computational modeling.

17. The bioreactor of claim 16, wherein the design comprises tunability.

18. The bioreactor of claim 16, wherein the design comprises peristalsis modeling that can mimic mechanical forces observed across multiple organ systems.

19. The bioreactor of claim 1, wherein mechanical forces are applied via the screw drive, and wherein the membrane is operable to receive and transmit the mechanical forces to biological elements.

20. A method of modeling peristalsis, the method comprising:

applying, via a screw drive, at least one of axial strain, multi-axial strain, or shear stress to a membrane within a bioreactor; and measuring, via piezoelectric hydrogels, mechanical forces applied to the membrane via the screw drive.

* * * * *